United States Patent [19]
Penner et al.

[11] Patent Number: 5,945,377
[45] Date of Patent: Aug. 31, 1999

[54] COMPOSITIONS CONTAINING HERBICIDE AND MONOSACCHARIDES AND METHOD OF USE THEREOF

[75] Inventors: Donald Penner, Williamston; Frank C. Roggenbuck, Lansing, both of Mich.

[73] Assignee: Board of Trustees operating Michigan State University, East Lansing, Mich.

[21] Appl. No.: 08/984,407

[22] Filed: Dec. 3, 1997

Related U.S. Application Data

[60] Provisional application No. 60/033,575, Dec. 6, 1996.

[51] Int. Cl.$^6$ .................................................. A01N 25/00
[52] U.S. Cl. ............................................................ 504/116
[58] Field of Search ............................................. 504/116

[56] References Cited

U.S. PATENT DOCUMENTS

| | | |
|---|---|---|
| 4,436,547 | 3/1984 | Sampson .................................. 71/76 |
| 4,617,049 | 10/1986 | Lengyel ..................................... 71/88 |

OTHER PUBLICATIONS

Nalewaja, J.D. et al, 1984, "Crop Origin Oils as Additives to Herbicides," Proceed. Ag–Chem . . . pp. 9–13.

Shasha, B.S. et al., 1976, "Starch–encap. Pesticides . . . ," Journal Polymer Science Polymer Lett. Ed. vol. 14, pp. 417–420.

Killick, R.W., et al., Proceedings North Central Weed . . . , vol. 50, pp. 117 (1995).

Thelen, K.D., et al., Weed Science, vol. 43, pp. 566–571 (1995).

*Primary Examiner*—S. Mark Clardy
*Attorney, Agent, or Firm*—Ian C. McLeod

[57] ABSTRACT

Compositions incorporating a postemergence herbicide and a monosaccharide, particularly fructose, as a potentiator of the herbicide against weeds without decreasing tolerance of a crop plant to the herbicide are described. The compositions are used as a spray in water in a method for killing weeds.

28 Claims, No Drawings

COMPOSITIONS CONTAINING HERBICIDE AND MONOSACCHARIDES AND METHOD OF USE THEREOF

CROSS-REFERENCE TO RELATED APPLICATION

This application claims the benefit of Provisional Application Serial No. 60/033,575, filed Dec. 6, 1996.

BACKGROUND OF THE INVENTION (1) Summary of the Invention

The present invention relates to herbicide compositions incorporating a monosaccharide, particularly fructose, as a potentiator for the herbicides in killing weeds without decreasing tolerance of the crop to the herbicide and to a method of use of the compositions. In particular, the present invention relates to compositions with the herbicide with the monosaccharide and adjuvants.

(2) Description of Related Art

Postemergence herbicides are well known to those skilled in the art. They include:
1. Nicosulfuron 2-[[[[(4,6-dimethoxy-2-pyrimidinyl)amino]carbonyl]amino]sulfonyl]-N,N-dimethyl-3-pyridinecarboxamide)—(ACCENT, Dupont, Wilmington, Del.)
2. Isopropylamine salt—glyphosate without adjuvants (ACCORD, Monsanto Company, St. Louis, Mo.)
3. Primisulfuron—(methyl 2-[[[[[4,6-bis(difluoromethoxy)-2-pyrimidinyl]amino]carbonyl]amino]sulfonyl]benzoate)— BEACON, Novartis, Greensboro, N.C.)
4. Chlorimuron ethyl—2-[[[[(4-chloro-6-methoxy-2-pyrimidinyl) amino]carbonyl]amino]sulfonyl]benzoate-ethyl (CLASSIC, Dupont, Wilmington, Del.)
5. Glufosinate-ammonium salt—(2-amino-4-(hydroxymethylphosphinyl)butanoic acid—(LIBERTY, AgrEvo, Wilmington, Del.)
6. Linuron—$N^1$-(3,4-dichlorophenyl)-N-methoxy-N-methylurea) (LOROX, Bayer, Kansas City, Kans.)
7. Linuron+chlorimuron ethyl—LOROX PLUS (DuPont, Wilmington, Del.)
8. Thifensulfuron—(methyl 3-[[[[(4-methoxy-6-methyl-1,3,5-triazin-2-yl]carbonyl]amino]sulfonyl]-2-thiophenecarboxylate) (PINNACLE, Dupont, Wilmington, Del.)
9. Imazethapyr—(PURSUIT, American Cyanamid, Princeton, N.J.)
10. Glyphosate-Isopropyl amine salt (N-(phosphonomethyl)glycine)(ROUNDUP, Monsanto Company, St. Louis, Mo.)
11. ROUND UP with surfactant components—phosphate esters and cationic tallow amines (ROUNDUP ULTRA, Monsanto, St. Louis, Mo.)
12. Imazaquin—(2-[4,5-dihydro-4-methyl-4-(1-methylethyl)-5-oxo-1H-imidazol-2-yl]-3-quinolinecarboxylic acid)—(SCEPTER, American Cyanamid, Princeton, N.J.)
13. Glyphosate-trimethylsulfonium salt (N-(phosphonomethyl)glycine)—(TOUCHDOWN, Zeneca Ag-Products, Wilmington, Del.)

For convenience, the trademarks are used in the specification, since those skilled in the art use them commonly. Also, the products can contain adjuvants as marketed.

In general, the herbicides are applied in aqueous solutions as a spray often containing ammonium sulfate or ammonium nitrate for hard water, and a surfactant as adjuvants. Various chemicals have been evaluated for efficacy as spray adjuvants for over a century (Gillette, C. P., "Experiments with Arsenates," Iowa Agricultural Experiment Station Bulletin, 10, pp. 401–420 (1890)). Early interest focused on petroleum based materials. In the last 15 years, there has been considerable interest in substituting adjuvants from renewable sources, such as vegetable oils or their derivatives, for petroleum-based chemicals (Nalewaja, J. D., et al., "Crop Origin Oils as Additives to Herbicides," Proceedings Ag-Chem Uses of Soybean Oil, American Soybean Association, St. Louis, Mo., pp. 9–13 (1984)). The perspective has broadened to the potential for use of value-added products from crops such as corn (Zea mays L.) in pesticide formulation or as spray additives. Corn starch encapsulated herbicide granules for controlled release formulations were developed by Shasha et al (Shasha, B. S., et al., Journal Polymer Science polymer Lett. Ed., Vol. 14, pp. 417–420 (1976)). Both corn oil and ethanol used for ethylating the corn oil have been used in an adjuvant developed for use with postemergence herbicides (Killick, R. W., et al., Proceedings North Central Weed Science Society, Vol. 50, pp.117 (1995)). Citric acid, which can be made from corn, has also been shown to serve as a chelator adjuvant immobilizing cations such as $Ca^{++}$, found in hard water that tend to form salts with anionic herbicides and reduce their absorption (Thelen, K. D., et al., Weed Science, Vol. 43, pp. 566–571 (1995)). Complex sugar containing molecules such as alkyl polyglycocides and sucroglycerides have been developed as spray adjuvants.

Imidazolinone-resistant corn varieties resistant to PURSUIT, carryover residues of SCEPTER, CLASSIC, or LOROX PLUS, and the interaction of COUNTER insecticide (terbufos (S-[[(1,1-dimethylethyl)thio]methyl]O,O-diethyl phosphorodithioate) (American Cyanamid, Princeton, N.J.) with BEACON or ACCENT are already in the marketplace. LIBERTY-resistant corn is scheduled for commercialization in 1997 and ROUNDUP-ready corn is scheduled for 1998. TOUCHDOWN can be used for burn-down in no-till corn. Both ROUNDUP ULTRA and TOUCHDOWN contain glyphosate as the active ingredient but they contain different salts, surfactant, or adjuvants.

DESCRIPTION OF PREFERRED EMBODIMENTS

The present invention relates to a composition which comprises an admixture: a postemergence herbicide which is effective against weeds growing with or without a crop plant; and an amount of a monosaccharide sufficient to potentiate the effect of the herbicide in killing the weeds without decreasing tolerance of the crop plant to the herbicide.

The present invention particularly relates to a synergistic composition which comprises an admixture: a postemergence herbicide which is effective against weeds growing with or without a crop plant; and (b) an amount of fructose sufficient to potentiate the effect of the herbicide in killing the weeds without decreasing tolerance of the crop plant to the herbicide.

The present invention also relates to a method for killing weeds growing with a crop plant the improvement which comprises: applying a composition comprising in admixture, a postemergence herbicide which is effective against weeds growing with or without a crop plant; and an amount of a monosaccharide sufficient to potentiate the effect of the herbicide in killing the weeds without decreasing tolerance of the crop plant to the herbicide.

The present invention particularly relates to a method for killing weeds growing with a crop plant the improvement which comprises: applying a composition comprising in admixture, a postemergence herbicide which is effective against weeds growing with or without a crop plant; and an amount of fructose sufficient to potentiate the effect of the herbicide in killing the weeds without decreasing tolerance of the crop plant to the herbicide.

The compositions of the present invention are preferably sold as a concentrate which is diluted with water, usually hard water in the field. The diluted composition provides sufficient herbicide to kill the weeds without affecting the crop. The amount is typically 0.01 to 4.0 kgha$^{-1}$ sprayed at 5 to 30 gpa in the dilute composition with some weeds requiring more herbicide than others. The herbicide is preferably an amino acid derivative.

The concentrate composition typically includes a metal ion (particularly Ca$^{++}$) binding agent, such as the preferred ammonium sulfate or ammonium nitrate, for hard water management. The metal binding agent is typically used in amounts up to about five percent (5%) weight per volume of the dilute composition to be applied, preferably between 0.5 and 3 percent.

The monosaccharide is used in amounts which potentiate the herbicide. Fructose is commercially available as syrups containing small amounts of water or as relatively dilute solutions containing 40 to 60% by weight fructose. The amount of the monosaccharide used is between about 0.1 and 5 percent weight per volume of the dilute composition. Most preferred is between 1 and 3 percent weight per volume.

Fructose which is preferred can be found with other chemicals. Typically fructose is produced from glucose using a glucose or xylose isomerase. The result is a mixed sugar solution which is predominantly fructose but also contains glucose. Various chemical and enzymatic processes are known for producing fructose. Preferred is corn syrup since it is a naturally derived source of fructose. Other monosaccharides can be used such as glucose or mannose. These are less preferred than corn syrup because of cost.

Surfactants and various vegetable oils or their esters are used to facilitate application of the herbicide to the weeds. The oils cause the herbicide to stay on the surface of the weeds and facilitate herbicide absorption. The oils and/or their esters are used in amounts between about 0.5 to 2.0 percent by weight to volume of the dilute composition. The composition typically includes a surfactant (cationic, neutral or anionic). These are used in amounts between about 0.1 and 2.0% by weight of the dilute composition. The surfactants aid in emulsifying an aqueous solution containing the oils to produce an oil-in-water emulsion. They can also be used independently at rates of 0.12 to 1.0% in the final spray solution.

The dilute compositions are applied as a spray. Typically the application is between about 5 to 30 gpa.

Corn syrup was evaluated as an adjuvant with several postemergence herbicides in the greenhouse and field studies in Examples 1 and 2. The greatest enhancement of herbicide activity was observed with high fructose corn syrup applied in combination with an ammonium sulfate and an effective nonionic adjuvant with anionic herbicides such as glyphosate and glufosinate for control of grass species such as giant foxtail. In the following Examples percentages are given by weight unless otherwise indicated.

EXAMPLE 1

Materials and Methods

Greenhouse Studies

Velvetleaf (*Abutilon theophrasti* Medicus), common lambsquarters (*Chenopodium album* L.), and giant foxtail (*Setaria faberi* Herrm.) were grown from seed in a BACCTO professional potting soil mix (Baccto Professional Planting Mix, Michigan Peat Company, Houston, Tex.) in 946-ml plastic pots. The pots were placed in the greenhouse at 25±2° C. with a 16-hr day/8-hr night. The pots were watered as needed, and after emergence, the plants were thinned to one plant per pot for the velvetleaf, two plants per pot for the common lambsquarters, and three plants per pot for the giant foxtail. Herbicides with adjuvants were applied when the plants were in the three- to four-leaf stage with a link-belt sprayer applying 236 L ha$^{-1}$ at 240 kPa. In all tests, the corn syrup applied was a specific high fructose (55% in water) corn syrup (ISOCLEAR 55, Cargill, Inc., Dayton Ohio) commonly used in the soft-drink industry. Preliminary studies evaluating various corn syrups identified this corn syrup as having the greatest efficacy as a herbicide adjuvant. The herbicides and other adjuvants are specified in the Tables. All application rates are specified in the Tables. In all greenhouse studies, plants were evaluated for herbicide injury and adjuvant efficacy 14 days after herbicide application. Data presented are the means of two experiments with four replications in each.

Various sugars were evaluated for efficacy as adjuvants with the acetolactate synthase (ALS)-inhibiting herbicide, primisulfuron (BEACON, Novartis, Greensboro, N.C.), fructose appeared to be more effective than glucose or sucrose (a disaccharide) in enhancing primisulfuron activity (Table 1).

TABLE 1

| | Adjuvant efficacy with primisulfuron 14 days after treatment | | |
|---|---|---|---|
| Treatment | Adjuvant | Velvetleaf | Giant foxtail |
| | | ---(% injury)--- | |
| Control | — | 0 h | 0 h |
| Primisulfuron[a] 14.8 g ha$^{-1}$ | — | 16 h | 14 g |
| Primisulfuron | + SCOIL (1%) + | 78 b | 79 a |
| | DASH[b] (1%) + | 56 c | 73 b |
| | X-77[c] (0.25%) + | 38 d | 63 c |
| | SYLGARD 309[d] (0.25%) + | 89 a | 64 c |
| | Dextrose (1% wt/vol) + | 23 fg | 34 e |
| | Fructose (1% wt/vol) + | 29 ef | 44 d |
| | Sucrose (1% wt/vol) + | 20 gh | 34 e |
| | Propylene glycol (1%) | 11 i | 24 f |

[a]Means for a given weed species with a common letter are not significantly different at the 5% level by the LSD test.
[b]DASH (BASF Corp., Research Triangle Park, NC); proprietary product.
[c]X-77 (Valent, Walnut Creek, CA); non-ionic surfactant which is a mixture of alkylarylpolyoxyethylene glycols, free fatty acids and isopropanol.
[d]SYLGARD 309 (Dow Corning, Midland, MI) heptamethylsiloxane Corn syrup at 1.25% in the spray solution was just as effective as if it was present at 2.5% for enhancing primisulfuron activity (TABLE 2).

TABLE 2

Adjuvant efficacy with primisulfuron 14 days after treatment

| Treatment | Adjuvant | Velvetleaf | Giant foxtail |
|---|---|---|---|
|  |  | ----(% injury)---- | |
| Control | — | 0 g | 0 f |
| Primisulfuron[a] 14.8 g ha$^{-1}$ | — | 16 f | 14 e |
| Primisulfuron | + SCOIL (1%)[b] + | 78 b | 79 a |
|  | DASH (1%) + | 56 c | 73 b |
|  | X-77 (0.25%) + | 38 d | 63 c |
|  | SYLGARD 309 (0.25%) + | 89 a | 64 c |
|  | Corn syrup (1.25%) + | 24 ef | 44 d |
|  | Corn syrup (2.5%) | 26 e | 45 d |

[a]Means for a given weed species with a common letter are not significantly different at the 5% level by the LSD test.
[b]See Table 1 for adjuvant compositions However, with nicosulfuron (ACCENT, Dupont, Wilmington, Del.), the 2.5% corn syrup enhanced herbicide activity on velvetleaf above that observed with 1.25% (Table 3).

TABLE 3

Adjuvant efficacy with nicosulfuron 14 days after treatment

| Treatment | Adjuvant | Velvetleaf | Giant foxtail |
|---|---|---|---|
|  |  | ----(% injury)---- | |
| Control | — | 0 e | 0 f |
| Nicosulfuron[a] 35 g ha-1b | — | 33 d | 23 e |
| Nicosulfuron | + SCOIL (1%)[c] + | 64 b | 78 a |
|  | DASH (1%) + | 48 c | 69 b |
|  | X-77 (0.25%) + | 44 c | 63 c |
|  | SYLGARD 309 (0.25%) + | 91 a | 58 c |
|  | Corn syrup (1.25%) + | 38 d | 29 d |
|  | Corn syrup (2.5%) | 45 c | 33 d |

[a]Means for a given weed species with a common letter are not significantly different at the 5% level by the LSD test.
[b]For giant foxtail, the rate was 3.5 g ha$^{-1}$
[c]See Table 1 for adjuvant compositions Although corn syrup enhanced the activity of these two herbicides it was less effective than other nonionic adjuvants tested. Corn syrup was also evaluated with the popular ALS-inhibitor, imazethapyr (PURSUIT, American Cyanamid, Princeton, N.J.). Both the ammonium nitrate in the UAN and the methylated seed oil in SUN-IT II (AGSCO, Grand Forks, ND) increased imazethapyr efficacy (Table 4).

TABLE 4

Adjuvant efficacy with imazethapyr 14 days after treatment

| Treatment | Adjuvant | Velvetleaf | Common lambs-quarters | Giant foxtail |
|---|---|---|---|---|
|  |  | -------------(% injury)-------------- | | |
| Control | — | 0 e | 0 e | 0 g |
| Imazethapyr[a] | — | 21 d | 11 d | 14 f |
| 24.6 g ha$^{-1}$ Imazethapyr | + SUN-IT II(1%) + 28% UAN (1%)[b] + | 48 b 47 b | 54 a 32 c | 71 c 35 e |
|  | SUN-IT II (1%) + 28% UAN (1%) + | 76 a | 56 a | 78 b |
|  | SUN-IT II (1%) + corn syrup (2%) + | 40 c | 43 b | 59 d |
|  | SUN-IT II (1%) + corn syrup (2%) + 28% UAN (1%) | 80 a | 55 a | 86 a |

[a]Means for a given weed species with a common letter are not significantly different at the 5% level by the LSD test.
[b]UAN—urea and ammonium nitrate Corn syrup further increased herbicide efficacy but only on the giant foxtail. The methylated seed oil adjuvants were very effective with the ALS inhibiting herbicides (Tables 1 to 4).

The corn syrup increased the activity of the isopropylamine salt of glyphosate (ROUNDUP, Monsanto Company, St. Louis, Mo.) from 12% control of giant foxtail to near 80% control (TABLE 5).

TABLE 5

Adjuvant efficacy with glyphosate (ROUNDUP) 14 days after treatment

| Treatment | Adjuvant | Velvetleaf | Giant foxtail |
|---|---|---|---|
|  |  | -----(% injury)----- | |
| Control | — | 0 d | 0 d |
| ROUNDUP[a] 0.28 kg ha$^{-1b}$ | — | 16 c | 12 c |
| ROUNDUP | + SCOIL (1%)[c] + | 24 b | 11 c |
|  | DASH (1%) + | 23 b | 11 c |
|  | X-77 (0.25%) + | 19 bc | 30 b |
|  | SYLGARD 309 (0.25%) + | 93 a | 78 a |
|  | Corn syrup (1.25%) + | 19 bc | 79 a |
|  | Corn syrup (2.5%) | 21 bc | 82 a |

[a]Means for a given weed species with a common letter are not significantly different at the 5% level by the LSD test.
[b]For giant foxtail, the rate was 0.22 kg ha$^{-1}$
[c]See Table 1 for compositions Enhancement of activity on velvetleaf was markedly increased with the organosilicone, SYLGARD 309. In a separate study, no difference in control of giant foxtail was observed between the ROUNDUP and the ROUNDUP ULTRA formulation of the isopropylamine salt of glyphosate applied with 2% ammonium sulfate. The addition of corn syrup to the ROUNDUP ULTRA formulation applied with 2% ammonium sulfate and 0.25% AMWAY 363566-P provided additional efficacy in giant foxtail control (TABLE 6).

TABLE 6

Adjuvant efficacy with glyphosate (ROUNDUP ULTRA)
14 days after treatment

| Treatment | Adjuvant | Velvetleaf | Common lambs-quarters | Giant foxtail |
|---|---|---|---|---|
| | | --------(% injury)-------- | | |
| ROUNDUP ULTRA[a,b] | — | 10 b | 34 c | 6 d |
| ROUNDUP ULTRA | + AMS (2%) + | 63 a | 63 b | 78 c |
| | AMS (2%) + corn syrup (1.25%) + | 69 a | 66 ab | 80 c |
| | Corn syrup (1.25%) + | 8 b | 63 b | 6 d |
| | AMS (2%) + Amway 363566-P (0.25%)[c] + | 73 a | 60 b | 91 b |
| | AMS (2%) + Amway 363566-P (0.25%) + corn syrup (1.25%) | 74 a | 73 a | 99 a |

[a]Means for a given weed species with a common letter are not significantly different at the 5% level by the LSD test.
[b]Velvetleaf 0.11 kg ha$^{-1}$, common lambsquarters 0.45 kg ha$^{-1}$, giant foxtail 0.17 kg ha$^{-1}$.
[c]AMS—Ammonium sulfate and AMWAY 363566-P, proprietary product, Amway, Ada, Michigan DASH HC plus 2% ammonium sulfate appeared to be an excellent adjuvant to enhance activity of the trimethylsulfonium salt of glyphosate (TABLE 7).

TABLE 7

Adjuvant efficacy with the trimethylsulfonium
salt of glyphosate (TOUCHDOWN)
14 days after treatment

| Treatment | Adjuvant | Velvetleaf | Common lambsquarters | Giant foxtail |
|---|---|---|---|---|
| | | --------(% injury)-------- | | |
| Glyphosate trimethyl-sulfonium[a,b] | — | 8 d | 18 c | 3 e |
| Glyphosate trimethyl-sulfonium | + AMS (2%) + | 76 a | 18 c | 55 c |
| | AMS (2%) + corn syrup (1.25%) + | 51 b | 19 c | 55 c |
| | Corn syrup (1.25%) + | 19 c | 18 c | 16 d |
| | AMS (2%) + DASH HC (1%) + | 83 a | 56 b | 81 b |
| | AMS (2%) + DASH HC (1%) + corn syrup (1.25%) | 81 a | 71 a | 93 a |

[a]Means for a given weed species with a common letter are not significantly different at the 5% level by the LSD test.
[b]Velvetleaf 0.11 kg ha$^{-1}$, common lambsquarters 0.45 kg ha$^{-1}$, giant foxtail 0.17 kg ha$^{-1}$.

The addition of corn syrup to this combination further enhanced activity on both common lambsquarters and giant foxtail (TABLE 7). Similar effects with corn syrup were observed with the combination of APSA-80 and 2% ammonium sulfate on the activity of glufosinate ammonium (LIBERTY) (TABLE 8).

TABLE 8

Adjuvant efficacy with glufosinate ammonium
14 days after treatment

| Treatment | Adjuvant | Velvetleaf | Common lambsquarters | Giant foxtail |
|---|---|---|---|---|
| | | ----------(% injury)---------- | | |
| Glufosinate ammonium[a,b,c] | — | 11 b | 21 d | 26 e |
| Glufosinate ammonium | + AMS (2%) + | 75 a | 53 b | 86 b |
| | AMS (2%) + corn syrup (1.25%) + | 81 a | 59 b | 98 a |
| | Corn syrup (1.25%) + | 14 b | 44 c | 74 c |
| | AMS (2%) + APSA-80 (0.25%) + | 75 a | 44 c | 64 d |
| | AMS (2%) + APSA-80 (0.25%) + corn syrup (1.25%) | 86 a | 79 a | 98 a |

[a]Means for a given weed species with a common letter are not significantly different at the 5% level by the LSD test.
[b]Velvetleaf 0.28 kg ha$^{-1}$, common lambsquarters 0.28 kg ha$^{-1}$, giant foxtail 0.17 kg ha$^{-1}$.
[c]APSA-80, proprietary formulation (Amway, Ada, Michigan)

The greenhouse studies indicate that corn syrup applied as an herbicide adjuvant increased activity on grasses but is best utilized in combination with an effective nonionic adjuvant.

In conclusion, corn syrup was most effective as an adjuvant to increase grass control if applied with an effective nonionic adjuvant plus 2% ammonium sulfate with glyphosate and glufosinate. The efficacy of the corn syrup as an adjuvant was both weed and herbicide specific.

EXAMPLE 2

The evaluation of corn syrup as an herbicide adjuvant in field trials was conducted on a field of HARRIS soft white winter wheat seeded in the fall of 1996 at East Lansing, Mich. When the wheat was in the five- to six-leaf stage in the spring of 1997, the isopropylamine salt of glyphosate (ROUNDUP ULTRA); the trimethylsulfonium salt of glyphosphate, TOUCHDOWN formulation; and the ammonium salt of glufosinate (LIBERTY) formulations were applied in spray solutions containing ammonium sulfate at 2% (wt/v) with or without the nonionic surfactant and with or without the corn syrup at 1.25% of Example 1. The application was at 190 L ha$^{-1}$ at 240 kPa. The herbicide rates and the specific nonionic adjuvants are specified in the Table. The plants in the pots were evaluated adjuvant efficacy manifest as herbicide injury 7, 14, and 24 days after herbicide.

All glyphosate treatments, regardless of adjuvant, totally controlled the wheat 21 days after treatment (data not presented). AMWAY 363566-P (Amway, Ada, Mich.) but not SCYTHE (Mycogen, San Diego, Calif.) appeared to be an effective adjuvant for glufosinate-ammonium (LIBERTY) (TABLE 9). The addition of corn syrup further enhanced the herbicide activity.

TABLE 9

The effect of high fructose corn syrup on glufosinate-ammonium (LIBERTY) efficacy on wheat in a field study in 1997

| Treatment | Adjuvant | 14 DAT | 21 DAT |
|---|---|---|---|
| | | ------(% injury)------- | |
| Untreated | — | 0 | 0 |
| Glufosinate ammonium[a] | | 61 | 33 |
| Glufosinate ammonium | + Corn syrup + | 70 | 52 |
| | Corn syrup + SCYTHE[b] + | 55 | 31 |
| | SCYTHE + | 37 | 19 |
| | Corn syrup + Amway 363566-P + | 72 | 52 |
| | Amway 363566-P | 65 | 43 |
| LSD$_{0.05}$ | | 6 | 7 |

[a]All glufosinate treatments received ammonium sulfate at 2%, the glufosinate rate 0.29 kg ha$^{-1}$, corn syrup (1.25%) and Amway 363566-P (0.25%), SCYTHE rate 1.0%.
[b]Pelargonic acid, Mycogen, San Diego, CA

EXAMPLE 3

The objects of this Example 3 were to: (a) determine the optimal adjuvants for the herbicides LIBERTY, TOUCHDOWN, and ROUNDUP ULTRA to control common weeds; and (b) evaluate high fructose corn syrups for efficacy to increase herbicide activity and possibly reduce drift.

EXPERIMENTAL PROCEDURES

Velvetleaf, common lambsquarters, and giant foxtail seeds obtained from V & J Seed Farms, Woodstock, Ill. were seeded into BACCTO professional potting mix in 1 quart plastic pots. The pots were placed in the greenhouse at 25±°C. with a 16 hr day, 8 hr night. After emergence the plants in the pots were thinned to one per pot for velvetleaf, two per pot for common lambsquarters, and three per pot for giant foxtail. Plants were fertilized and watered as needed. When the weeds were at the 3- to 4-leaf stage, they were sprayed with the various herbicide and adjuvant treatments in a spray system that delivered 25 gal/acre at 25 psi. The weeds were evaluated for herbicide injury (weed control) 14 days after treatment.

RESULTS AND DISCUSSION

In the absence of an added adjuvant, no difference was observed in giant foxtail control between ROUNDUP and ROUNDUP ULTRA applied at 0.5 and 1 pt/acre. The addition of 2% ammonium sulfate to spray solution used with ROUNDUP ULTRA, LIBERTY, and TOUCHDOWN greatly increased herbicide activity on velvetleaf, common lambsquarters and giant foxtail with one exception, it did not increase TOUCHDOWN activity on common lambsquarters. Most herbicide applications are made using hard water, a condition virtually requiring the use of ammonium sulfate with certain herbicides including the ones tested in this Example. Of the various adjuvants evaluated, only AMWAY 363566-P enhanced LIBERTY and ROUNDUP ULTRA activity beyond the increase obtained with ammonium sulfate on common lambsquarters and giant foxtail, respectively. Most of the adjuvants evaluated increased TOUCHDOWN activity. The best two adjuvants across weed species were AMWAY 363566-P and DASH HC. The further addition of CARGILL ISOCLEAR 55 high fructose corn syrup to the spray solutions containing TOUCHDOWN, ammonium sulfate, plus a surfactant type adjuvant provided significantly greater activity on giant foxtail and occasionally on common lambsquarters. This combination effect of ISOCLEAR 55 in increasing giant foxtail control when applied with a surfactant type adjuvant was also evident with LIBERTY and ROUNDUP ULTRA.

TABLE 10

The efficacy of selected adjuvants with TOUCHDOWN herbicide

| | Visual injury[a] (%) | | |
|---|---|---|---|
| Treatment[b] | Velvetleaf | Common lambsquarters | Giant foxtail |
| 1. TOUCHDOWN alone[c] | 8 m | 18 m | 3 n |
| 2. TOUCHDOWN + AMS | 76 b–f | 18 m | 55 l |
| 3. TOUCHDOWN + AMS + ISOCLEAR 55 | 51 j | 19 m | 55 l |
| 4. TOUCHDOWN + ISOCLEAR 55 | 19 l | 18 m | 16 m |
| 5. TOUCHDOWN + AMS + HASTEN (1%)[d] | 71 e–i | 41 l | 78 gh |
| 6. TOUCHDOWN + AMS + HASTEN (1%) + ISOCLEAR 55 | 78 b–e | 52 efg | 83 def |
| 7. TOUCHDOWN + AMS + SYLGARD 309 (0.25%) | 88 a | 41 l | 59 kl |
| 8. TOUCHDOWN + AMS + SYLGARD 309 + ISOCLEAR 55 | 68 f–i | 47 h–k | 82 d–g |
| 9. TOUCHDOWN + AMS + APSA-80 (0.25%) | 73 d–h | 50 f–i | 73 i |
| 10. TOUCHDOWN + AMS + APSA-80 (0.25%) + ISOCLEAR 55 | 73 d–h | 59 c | 86 cd |
| 11. TOUCHDOWN + AMS + DC 212 (0.25%)[d] | 71 e–i | 4 jkl | 64 j |
| 12. TOUCHDOWN + AMS + DC 212 (0.25%) + ISOCLEAR 55 | 76 b–f | 53 def | 84 cde |
| 13. TOUCHDOWN + AMS + SCOIL (1%) | 70 e–i | 46 i–l | 74 hi |
| 14. TOUCHDOWN + AMS + SCOIL (1%) + ISOCLEAR 55 | 76 b–f | 57 cd | 84 cde |
| 15. TOUCHDOWN + AMS + PREFERENCE (1%)[d] | 73 d–h | 58 c | 79 fg |
| 16. TOUCHDOWN + AMS + PREFERENCE (1%) + ISOCLEAR 55 | 74 c–g | 59 c | 88 bc |
| 17. TOUCHDOWN + AMS + DASH HC (1%) | 83 ab | 56 cde | 81 efg |
| 18. TOUCHDOWN + AMS + DASH HC (1%) + ISOCLEAR 55 | 81 abc | 71 a | 93 ab |
| 19. TOUCHDOWN + AMS + AMWAY 363566 P (0.25%) | 88 a | 68 ab | 86 cd |
| 20. TOUCHDOWN + AMS + AMWAY 363566 P (0.25%) + ISOCLEAR 55 | 80 a–d | 71 a | 92 ab |
| 21. TOUCHDOWN + AMS + SCYTHE (1%) | 41 k | 43 kl | 60 jk |
| 22. TOUCHDOWN + AMS + SCYTHE (1%) + ISOCLEAR 55 | 65 hi | 66 b | 95 a |
| 23. Non-treated Control | 0 m | 0 n | 0 n |
| LSD$_{0.05}$ | 8.3 | 4.4 | 4.8 |

[a]Data are the means of two experiments with four replications each.
[b]TOUCHDOWN rates: 0.10 lb/A for velvetleaf, 0.40 lb/A for common lambsquarters, 0.15 lb/A for giant foxtail, ammonium sulfate (AMS) rate is 2% wt/vol; ISOCLEAR 55 rate 1.25%; applied at 25 gpa.
[c]Means for a given weed species with a common letter are not significantly different at the 5% level of the LSD test.
[d]PREFERENCE proprietary formulation (Cenex/Land O'Lakes, Invergrove Heights, MN);
HASTEN proprietary formulation (Wilfarm, Fresno, CA);
DC212 proprietary formulation (Dow Corning, Midland, MI)—For other adjuvant formulations, see earlier Tables.

TABLE 11

The efficacy of selected adjuvants with ROUNDUP ULTRA herbicide

| Treatment[b] | Visual injury[a] Velvetleaf | Common Lambsquarters (%) | Giant foxtail |
|---|---|---|---|
| 1. ROUNDUP ULTRA alone[c] | 10 h | 34 l | 6 j |
| 2. ROUNDUP ULTRA + AMS | 63 a–g | 63 b–e | 78 fg |
| 3. ROUNDUP ULTRA + AMS + ISOCLEAR 55 | 69 a–d | 66 a–d | 80 efg |
| 4. ROUNDUP ULTRA + ISOCLEAR 55 | 8 h | 63 b–e | 6 j |
| 5. ROUNDUP ULTRA + AMS + HASTEN (1%) | 69 a–d | 38 kl | 72 hi |
| 6. ROUNDUP ULTRA + AMS + HASTEN (1%) + ISOCLEAR 55 | 61 d–g | 56 fgh | 91 cd |
| 7. ROUNDUP ULTRA + AMS + SYLGARD 309 (0.25%) | 61 d–g | 34 l | 71 i |
| 8. ROUNDUP ULTRA + AMS + SYLGARD 309 (0.25%) + ISOCLEAR 55 | 68 a–e | 40 jkl | 82 ef |
| 9. ROUNDUP ULTRA + AMS + APSA-80 (0.25%) | 68 a–e | 52 hi | 77 fgh |
| 10. ROUNDUP ULTRA + AMS + APSA-80 (0.25%) + ISOCLEAR 55 | 68 a–e | 69 ab | 84 e |
| 11. ROUNDUP ULTRA + AMS + DC 212 (0.25%) | 63 a–g | 46 ij | 78 fg |
| 12. ROUNDUP ULTRA + AMS + DC 212 (0.25%) + ISOCLEAR 55 | 58 efg | 53 h | 96 ab |
| 13. ROUNDUP ULTRA + AMS + SCOIL (1%) | 61 d–g | 42 jk | 70 i |
| 14. ROUNDUP ULTRA + AMS + SCOIL (1%) + ISOCLEAR 55 | 62 c–g | 54 gh | 91 cd |
| 15. ROUNDUP ULTRA + AMS + PREFERENCE (1%) | 57 fg | 58 e–h | 79 fg |
| 16. ROUNDUP ULTRA + AMS + PREFERENCE (1%) + ISOCLEAR 55 | 54 g | 68 abc | 95 abc |
| 17. ROUNDUP ULTRA + AMS + DASH HC (1%) | 61 d–g | 53 h | 76 gh |
| 18. ROUNDUP ULTRA + AMS + DASH HC (1%) + ISOCLEAR 55 | 68 a–e | 60 d–g | 93 bcd |
| 19. ROUNDUP ULTRA + AMS + AMWAY P (0.25%) | 73 ab | 60 d–g | 91 cd |
| 20. ROUNDUP ULTRA + AMS + AMWAY P (0.25%) + ISOCLEAR 55 | 74 a | 73 a | 99 a |
| 21. ROUNDUP ULTRA + AMS + SCYTHE (1%) | 64 a–g | 36 kl | 72 hi |
| 22. ROUNDUP ULTRA + AMS + SCYTHE (1%) + ISOCLEAR 55 | 73 ab | 54 gh | 99 a |
| 23. Non-treated Control | 0 h | 0 m | 0 k |
| LSD$_{0.05}$ | 11.1 | 6.3 | 5.3 |

[a]Data are the means of two experiments with four replications each.
[b]ROUNDUP ULTRA rates: 0.10 lb/A for velvetleaf, 0.40 lb/A for common lambsquarters, 0.15 lb/A for giant foxtail, ammonium sulfate (AMS) rate is 2% wt/vol; ISOCLEAR 55 rate 1.25%; applied at 25 gpa.
[c]Means for a given weed species with a common letter are not significantly different at the 5% level of the LSD test.

TABLE 12

The efficacy of selected adjuvants with LIBERTY herbicide

| Treatment[b] | Visual injury[a] Velvetleaf | Common Lambsquarters (%) | Giant foxtail |
|---|---|---|---|
| 1. LIBERTY alone | 11 j | 21 lmn | 26 n |
| 2. LIBERTY + AMS | 75 de | 53 cd | 86 ef |
| 3. LIBERTY + AMS + ISOCLEAR 55 | 81 a–d | 59 bc | 98 ab |
| 4. LIBERTY + ISOCLEAR 55 | 14 j | 44 ef | 74 h |
| 5. LIBERTY + AMS + HASTEN (1%) | 65 fgh | 18 mn | 41 m |
| 6. LIBERTY + AMS + HASTEN (1%) + ISOCLEAR 55 | 84 abc | 30 h–k | 63 jk |
| 7. LIBERTY + AMS + SYLGARD 309 (0.25%) | 64 gh | 13 n | 43 m |
| 8. LIBERTY + AMS + SYLGARD 309 (0.25%) + ISOCLEAR 55 | 89 a | 14 n | 71 h |
| 9. LIBERTY + AMS + APSA-80 (0.25%) | 75 de | 44 ef | 64 ij |
| 10. LIBERTY + AMS + APSA-80 + ISOCLEAR 55 | 86 ab | 79 a | 98 ab |
| 11. LIBERTY + AMS + DC 212 (0.25%) | 58 hi | 28 i–l | 69 hi |
| 12. LIBERTY + AMS + DC 212 (0.25%) + ISOCLEAR 55 | 71 efg | 31 g–j | 100 a |
| 13. LIBERTY + AMS + SCOIL (1%) | 66 fg | 23 klm | 40 m |
| 14. LIBERTY + AMS + SCOIL (1%) + ISOCLEAR 55 | 79 b–e | 36 f–i | 85 fg |
| 15. LIBERTY + AMS + PREFERENCE (1%) | 64 gh | 24 j–m | 58 kl |
| 16. LIBERTY + AMS + PREFERENCE (1%) + ISOCLEAR 55 | 78 cde | 41 f | 80 g |
| 17. LIBERTY + AMS + DASH HC (1%) | 73 ef | 37 fgh | 53 l |
| 18. LIBERTY + AMS + DASH HC (1%) + ISOCLEAR 55 | 84 abc | 50 de | 91 cde |
| 19 LIBERTY + AMS + AMWAY 363566 P (0.25%) | 83 a–d | 66 b | 88 def |
| 20. LIBERTY + AMS + AMWAY 363566 P (0.25%) + ISOCLEAR 55 | 86 ab | 85 a | 100 a |
| 21. LIBERTY + AMS + SCYTHE (1%) | 75 de | 21 lmn | 73 h |
| 22. LIBERTY + AMS + SCYTHE (1%) + ISOCLEAR 55 | 88 a | 38 fgh | 93 bcd |
| 23. Non-treated Control | 0 k | 0 o | 0 o |
| LSD$_{0.05}$ | 7.5 | 8.5 | 6.2 |

[a]Data are the means of two experiments with four replications each.
[b]LIBERTY rates: 0.25 lb/A for velvetleaf and common lambsquarters, 0.15 lb/A for giant foxtail, ammonium sulfate (AMS) rate is 2% wt/vol; ISOCLEAR 55 rate 1.25%; applied at 25 gpa.
[c]Means for a given weed species with a common letter are not significantly different at the 5% level of the LSD test.

TABLE 13

Corn Product Based Herbicide Adjuvants: ROUNDUP on giant foxtail

| Treatment | | Visual injury (14 DAT)[b] (%) |
|---|---|---|
| 1. Non-treated control | | 0 m |
| 2. ROUNDUP alone | (0.2 lb/A) | 12 l |
| 3. ROUNDUP + SCOIL | (1%) | 11 l |
| 4. ROUNDUP + DASH | (1%) | 11 l |
| 5. ROUNDUP + X-77 | (0.25%) | 30 k |
| 6. ROUNDUP + SYLGARD 309 | (0.25%) | 78 bcd |
| 7. ROUNDUP + Dextrose | (1% wt/vol) | 77 b-e |
| 8. ROUNDUP + Fructose | (1% wt/vol) | 84 a |
| 9. ROUNDUP + Sucrose | (1% wt/vol) | 69 f-i |
| 10. ROUNDUP + Propylene glycol | (1%) | 16 l |
| 11. ROUNDUP + CARGILL CRGX[a] 4306 (60% dextrose; 40% H$_2$O) | (1.25% wt/vol) | 78 bcd |
| 12. ROUNDUP + CARGILL CRGX 4306 (60% dextrose; 40% H$_2$O) | (2.5% wt/vol) | 73 def |
| 13. ROUNDUP + CARGILL ISOCLEAR 42 | (1.25% wt/vol) | 76 cde |
| 14. ROUNDUP + CARGILL ISOCLEAR 42 (42% Fructose) | (2.5% wt/vol) | 70 fgh |
| 15. ROUNDUP + CARGILL ISOCLEAR 55 | (1.25% wt/vol) | 79 bc |
| 16. ROUNDUP + CARGILL ISOCLEAR 55 (55% Fructose) | (2.5% wt/vol) | 82 ab |
| 17. ROUNDUP + Cargill CRGX 5290 (high dextrose syrup) | (1.25% wt/vol) | 62 j |
| 18. ROUNDUP + CARGILL CRGX 5290 (high dextrose syrup) | (2.5% wt/vol) | 67 g-j |
| 19. ROUNDUP + CARGILL 43/43 - 19% dextrose; 14% maltose; 12% maltothiose; 55% higher saccharides | (1.25% wt/vol) | 66 hij |
| 20. ROUNDUP + CARGILL 43/43 - 19% dextrose; 14% maltose; 12% maltothiose; 55% higher saccharides | (2.5% wt/vol) | 64 ij |
| 21. ROUNDUP + CARGILL 63/43; 36% dextrose; 31% maltose | (1.25% wt/vol) | 72 efg |
| 22. ROUNDUP + CARGILL 63/43 (36% dextrose; 31% maltose | (2.5% wt/vol) | 76 cde |
| LSD$_{0.05}$ | | 5.3 |

[a]CARGILL, Dayton, OH.
[b]Means for a given weed species with a common letter are not significantly different at the 5% level by the LSD test.

TABLE 14

PURSUIT and SCYTHE interactions on velvetleaf, giant foxtail, and common lambsquarters

| | Visual injury (14 DAT)[b] | | |
|---|---|---|---|
| Treatment[a] | Velvetleaf | Giant foxtail | Common lambsquarter |
| | ----------(%)------------ | | |
| 1. Non-treated control | 0 h | 0 i | 0 g |
| 2. PURSUIT (0.022 lb/A) | 21 g | 14 h | 11 f |
| 3. PURSUIT (0.022 lb/A) + SUN-IT II (1%) | 48 c | 71 cd | 54 ab |
| 4. PURSUIT (0.022 lb/A) + 28% UAN (1%) | 47 cd | 35 g | 32 d |
| 5. PURSUIT (0.022.lb/A) + SUN-IT II (1%) + 28% UAN (1%) | 76 a | 78 b | 56 a |
| 6. PURSUIT (0.022 lb/A + SUN-IT II (1%) + ISOCLEAR 55 (2%) | 40 e | 59 e | 43 c |
| 7. PURSUIT (0.022 lb/A + SUN-IT II (1%) + ISOCLEAR 55 (2%) + 28% UAN (1%) | 80 a | 86 a | 55 a |
| 8. SCYTHE (1%) | 0 h | 0 i | 0 g |
| 9. PURSUIT (0.022 lb/A) + SCYTHE (1%) | 39 e | 54 f | 51 b |
| 10. PURSUIT (0.022 lb/A) + SCYTHE (1%) + 28% UAN (1%) | 69 b | 74 bc | 58 a |
| 11. PURSUIT (0.022 lb/A) + SCYTHE (1%) + ISOCLEAR 55 (2%) | 43 de | 69 d | 43 c |
| 12. PURSUIT (0.022 lb/A) + SCYTHE (1%) + ISOCLEAR 55 (2%) + 28% UAN (1%) | 70 b | 85 a | 56 a |
| 13. PURSUIT (0.022 lb/A) + ISOCLEAR 55 (2%) | 30 f | 39 g | 26 e |
| LSD$_{0.05}$ | 4.0 | 4.1 | 4.3 |

[a]Means are from two experiments with four replications each; applied at 25 gpa; leaf stages: velvetleaf 5, giant foxtail 3, common lambsquarters 5.
[b]Means for a given weed species with a common letter are not significantly different at the 5% level by the LSD test.

TABLE 15

PURSUIT and SCYTHE interactions on RESNIK soybean

| | Visual injury[b] | |
|---|---|---|
| Treatment[a] | 7 DAT | 14 DAT |
| | ----(%)---- | |
| 1. Nontreated control | 0 h | 0 f |
| 2. PURSUIT (0.022 lb/A) | 7 f | 0 f |
| 3. PURSUIT (0.022 lb/A) + SUN-IT II (1%) | 13 d | 1 ef |
| 4. PURSUIT (0.022 lb/A) + 28% UAN (1%) | 9 ef | 4 d |
| 5. PURSUIT (0.022 lb/A) + SUN-IT II (1%) + 28% UAN (1%) | 21 b | 10 bc |
| 6. PURSUIT (0.022 lb/A) + SUN-IT II (1%) + ISOCLEAR 55 (2%) | 17 c | 8 c |
| 7. PURSUIT (0.022 lb/A) + SUN-IT II (1%) + ISOCLEAR 55 (2%) + 28% UAN (1%) | 19 bc | 11 ab |
| 8. SCYTHE (1%) | 1 gh | 0 f |
| 9 PURSUIT (0.022 lb/A) + SCYTHE (1%) | 11 de | 3 de |
| 10. PURSUIT (0.022 lb/A) + SCYTHE (1%) + 28% UAN (1%) | 24 a | 13 a |
| 11. PURSUIT (0.022 lb/A) + SCYTHE (1%) + ISOCLEAR 55 (2%) | 17 c | 10 bc |
| 12. PURSUIT (0.022 lb/A) + SCYTHE (1%) + ISOCLEAR 55 (2%) + 28% UAN (1%) | 26 a | 13 a |
| 13. PURSUIT (0.022 lb/A) + ISOCLEAR 55 (2%) | 3 g | 0 f |
| LSD$_{0.05}$ | 2.5 | 2.0 |

[a]Means are from two experiments with four replications each; applied at 25 gpa; leaf stage: first trifoliolate.
[b]Means for a given date with a common letter are not significantly different at the 5% level by the LSD test.

TABLE 16

Corn Product Based Herbicide Adjuvants: ROUNDUP on velvetleaf.

| Treatment | Adjuvant Rate | Visual Injury (14 DAT) (%) |
|---|---|---|
| 1. Non-treated control | | 0 k |
| 2. ROUNDUP alone (0.25 lb/A) | | 16 fgh |
| 3. ROUNDUP + SCOIL | (1%) | 24 cd |
| 4. ROUNDUP + DASH | (1%) | 23 cde |

TABLE 16-continued

Corn Product Based Herbicide Adjuvants: ROUNDUP on velvetleaf.

| Treatment | Adjuvant Rate | Visual Injury (14 DAT) (%) |
|---|---|---|
| 5. ROUNDUP + X-77 | (0.25%) | 19 def |
| 6. ROUNDUP + SYLGARD 309 | (0.25%) | 93 a |
| 7. ROUNDUP + Dextrose | (1% wt/vol) | 28 bc |
| 8. ROUNDUP + Fructose | (1% wt/vol) | 30 b |
| 9. ROUNDUP + Sucrose | (1% wt/vol) | 13 ghi |
| 10. ROUNDUP + Propylene glycol | (1%) | 4 jk |
| 11. ROUNDUP + CARGILL CRGX 4306 | (1.25% wt/vol) | 11 hi |
| 12. ROUNDUP + CARGILL CRGX 4306 | (2.5% wt/vol) | 18 efg |
| 13. ROUNDUP + CARGILL ISOCLEAR 42 | (1.25% wt/vol) | 18 efg |
| 14. ROUNDUP + CARGILL ISOCLEAR 42 | (2.5% wt/vol) | 15 fgh |
| 15. ROUNDUP + CARGILL ISOCLEAR 55 | (1.25% wt/vol) | 19 def |
| 16. ROUNDUP + CARGILL ISOCLEAR 55 | (2.5% wt/vol) | 21 def |
| 17. ROUNDUP + CARGILL CRGX 5290 | (1.25% wt/vol) | 9 ij |
| 18. ROUNDUP + CARGILL CRGX 5290 | (2.5% wt/vol) | 5 jk |
| 19. ROUNDUP + CARGILL 43/43 | (1.25% wt/vol) | 8 ij |
| 20. ROUNDUP + CARGILL 43/43 | (2.5% wt/vol) | 8 ij |
| 21. ROUNDUP + CARGILL 63/43 | (1.25% wt/vol) | 5 jk |
| 22. ROUNDUP + CARGILL 63/43 | (2.5% wt/vol) | 13 ghi |
| $LSD_{0.05}$ | | 5.7 |

TABLE 17

Corn Product Based Herbicide Adjuvants: BEACON on giant foxtail

| Treatment | Adjuvant Rate | Visual injury (14 DAT) (%) |
|---|---|---|
| 1. Non-treated control | | 0 j |
| 2. BEACON alone (0.0132 lb/A) | | 14 i |
| 3. BEACON + SCOIL | 1% | 79 a |
| 4. BEACON + DASH | 1% | 73 b |
| 5. BEACON + X-77 | 0.25% | 63 c |
| 6. BEACON + SYLGARD 309 | 0.25% | 64 c |
| 7. BEACON + Dextrose | 1% wt/vol | 34 g |
| 8. BEACON + Fructose | 1% wt/vol | 44 def |
| 9. BEACON + Sucrose | 1% wt/vol | 34 g |
| 10. BEACON + Propylene glycol | 1% | 24 h |
| 11. BEACON + CARGILL CRGX 4306 | 1.25% wt/vol | 41 ef |
| 12. BEACON + CARGILL CRGX4306 | 2.5% wt/vol | 46 de |
| 13. BEACON + CARGILL ISOCLEAR 42 | 1.25% wt/vol | 45 de |
| 14. BEACON + CARGILL ISOCLEAR 42 | 2.5% wt/vol | 49 d |
| 15. BEACON + CARGILL ISOCLEAR 55 | 1.25% wt/vol | 44 def |
| 16. BEACON + CARGILL ISOCLEAR 55 | 2.5% wt/vol | 45 de |
| 17. BEACON + CARGILL CRGX 5290 | 1.25% wt/vol | 39 fg |
| 18 BEACON + CARGILL CRGX 5290 | 2.5% wt/vol | 35 g |
| 19 BEACON + CARGILL 43/43 | 1.25% wt/vol | 35 g |
| 20. BEACON + CARGILL 43/43 | 2.5% wt/vol | 34 g |
| 21. BEACON + CARGILL 63/43 | 1.25% wt/vol | 41 ef |
| 22. BEACON + CARGILL 63/43 | 2.5% wt/vol | 41 ef |
| $LSD_{0.05}$ | | 6.0 |

TABLE 18

Corn Product Based Herbicide Adjuvants: BEACON on velvetleaf.

| Treatment | Adjuvant Rate | Visual injury (14 DAT) (%) |
|---|---|---|
| 1. Non-treated control | | 0 l |
| 2. BEACON alone (0.0132 lb/A) | | 16 h–k |
| 3. BEACON + SCOIL | 1% | 78 b |
| 4. BEACON + DASH | 1% | 56 c |
| 5. BEACON + X-77 | 0.25% | 38 d |
| 6. BEACON + SYLGARD 309 | 0.25% | 89 a |
| 7. BEACON + Dextrose | 1% wt/vol | 23 f–i |
| 8. BEACON + Fructose | 1% wt/vol | 29 ef |
| 9. BEACON + Sucrose | 1% wt/vol | 20 g–j |
| 10. BEACON + Propylene glycol | 1% | 11 k |
| 11. BEACON + CARGILL CRGX 4306 | 1.25% wt/vol | 18 h–k |
| 12. BEACON + CARGILL CRGX 4306 | 2.5% wt/vol | 23 fgh |
| 13. BEACON + CARGILL ISOCLEAR 42 | 1.25% wt/vol | 15 ijk |
| 14. BEACON + CARGILL ISOCLEAR 42 | 2.5% wt/vol | 28 efg |
| 15. BEACON + CARGILL ISOCLEAR 55 | 1.25% wt/vol | 24 e–h |
| 16. BEACON + CARGILL ISOCLEAR 55 | 2.5% wt/vol | 26 efg |
| 17. BEACON + CARGILL CRGX 5290 | 1.25% wt/vol | 18 h–k |
| 18. BEACON + CARGILL CRGX 5290 | 2.5% wt/vol | 15 ijk |
| 19. BEACON + CARGILL 43/43 | 1.25% wt/vol | 16 h–k |
| 20. BEACON + CARGILL 43/43 | 2.5% wt/vol | 14 jk |
| 21. BEACON + CARGILL 63/43 | 1.25% wt/vol | 20 g–j |
| 22. BEACON + CARGILL 63/43 | 2.5% wt/vol | 31 de |
| $LSD_{0.05}$ | | 8.1 |

TABLE 19

Corn Product Based Herbicide Adjuvants: ACCENT on giant foxtail.

| Treatment | Adjuvant Rate | Visual injury (14 DAT) (%) |
|---|---|---|
| 1. Non-treated control | | 0 j |
| 2. ACCENT alone (0.0031 lb/A) | | 23 hi |
| 3. ACCENT + SCOIL | 1% | 78 a |
| 4. ACCENT + DASH | 1% | 69 b |
| 5. ACCENT + X-77 | 0.25% | 63 c |
| 6. ACCENT + SYLGARD 309 | 0.25% | 58 c |
| 7. ACCENT + Dextrose | 1% wt/vol | 26 f–i |
| 8. ACCENT + Fructose | 1% wt/vol | 34 d |
| 9. ACCENT + Sucrose | 1% wt/vol | 23 hi |
| 10. ACCENT + Propylene glycol | 1% | 21 i |
| 11. ACCENT + CARGILL CRGX 4306 | 1.25% wt/vol | 28 e–h |
| 12. ACCENT + CARGILL CRGX 4306 | 2.5% wt/vol | 26 f–i |
| 13. ACCENT + CARGILL ISOCLEAR 42 | 1.25% wt/vol | 31 def |
| 14. ACCENT + CARGILL ISOCLEAR 42 | 2.5% wt/vol | 31 def |
| 15. ACCENT + CARGILL ISOCLEAR 55 | 1.25% wt/vol | 29 d–g |
| 16. ACCENT + CARGILL ISOCLEAR 55 | 2.5% wt/vol | 33 de |
| 17. ACCENT + CARGILL CRGX 5290 | 1.25% wt/vol | 24 ghi |
| 18. ACCENT + CARGILL CRGX 5290 | 2.5% wt/vol | 29 d–g |
| 19. ACCENT + CARGILL 43/43 | 1.25% wt/vol | 26 f–i |
| 20. ACCENT + CARGILL 43/43 | 2.5% wt/vol | 23 hi |
| 21. ACCENT + CARGILL 63/43 | 1.25% wt/vol | 24 ghi |
| 22. ACCENT + CARGILL 63/43 | 2.5% wt/vol | 26 f–i |
| $LSD_{0.05}$ | | 6.1 |

TABLE 20

Corn Product Based Herbicide Adjuvants: ACCENT on velvetleaf.

| Treatment | Adjuvant Rate | Visual injury (14 DAT) (%) |
|---|---|---|
| 1. Non-treated control | | 0 k |
| 2. ACCENT alone (0.031 lb/A) | | 33 fgh |

TABLE 20-continued

Corn Product Based Herbicide Adjuvants:
ACCENT on velvetleaf.

| Treatment | Adjuvant Rate | Visual injury (14 DAT) (%) |
|---|---|---|
| 3. ACCENT + SCOIL | 1% | 64 b |
| 4. ACCENT + DASH | 1% | 48 c |
| 5. ACCENT + X-77 | 0.25% | 44 cd |
| 6. ACCENT + SYLGARD 309 | 0.25% | 91 a |
| 7. ACCENT + Dextrose | 1% wt/vol | 36 efg |
| 8. ACCENT + Fructose | 1% wt/vol | 41 de |
| 9. ACCENT + Sucrose | 1% wt/vol | 25 j |
| 10. ACCENT + Propylene glycol | 1% | 31 ghi |
| 11. ACCENT + CARGILL CRGX 4306 | 1.25% wt/vol | 25 j |
| 12. ACCENT + CARGILL CRGX 4306 | 2.5% wt/vol | 28 hij |
| 13. ACCENT + CARGILL ISOCLEAR 42 | 1.25% wt/vol | 27 hij |
| 14. ACCENT + CARGILL ISOCLEAR 42 | 2.5% wt/vol | 33 fgh |
| 15. ACCENT + CARGILL ISOCLEAR 55 | 1.25% wt/vol | 38 ef |
| 16. ACCENT + CARGILL ISOCLEAR 55 | 2.5% wt/vol | 45 cd |
| 17. ACCENT + CARGILL CRGX 5290 | 1.25% wt/vol | 29 hij |
| 18 ACCENT + CARGILL CRGX 5290 | 2.5% wt/vol | 28 hij |
| 19. ACCENT + CARGILL 43/43 | 1.25% wt/vol | 29 hij |
| 20. ACCENT + CARGILL 43/43 | 2.5% wt/vol | 28 hij |
| 21. ACCENT + CARGILL 63/43 | 1.25% wt/vol | 26 ij |
| 22. ACCENT + CARGILL 63/43 | 2.5% wt/vol | 25 j |
| $LSD_{0.05}$ | | 5.6 |

TABLE 21

Corn Product Based Herbicide Adjuvants:
PINNACLE on common lambsquarters.

| | | Visual injury (14 DAT) | |
|---|---|---|---|
| Treatment | Adjuvant Rate | No DASH | Plus DASH (1%) |
| 1. Non-treated control | | 0 n | — |
| 2. PINNACLE alone (0.0016 lb/A) | | 11 lm | — |
| 3. PINNACLE + SCOIL | 1% | 74 a–f | — |
| 4. PINNACLE + DASH | 1% | 76 abc | — |
| 5. PINNACLE + X-77 | 0.25% | 69 efg | — |
| 6. PINNACLE + SYLGARD 309 | 0.25% | 67 g | — |
| 7. PINNACLE + Dextrose | 1% wt/vol | 13 klm | 78 a |
| 8. PINNACLE + Fructose | 1% wt/vol | 20 i | 76 abc |
| 9. PINNACLE + Sucrose | 1% wt/vol | 18 ijk | 71 c–g |
| 10. PINNACLE + Propylene glycol | 1% | 28 h | 71 c–g |
| 11. PINNACLE + CARGILL CRGX 4306 | 1.25% wt/vol | 16 i–l | 75 a–e |
| 12. PINNACLE + CARGILL CRGX 4306 | 2.5% wt/vol | 14 jkl | 74 a–f |
| 13. PINNACLE + CARGILL ISOCLEAR 42 | 1.25% wt/vol | 13 klm | 70 d–g |
| 14. PINNACLE + CARGILL ISOCLEAR 42 | 2.5% wt/vol | 16 i–l | 78 ab |
| 15. PINNACLE + CARGILL ISOCLEAR 55 | 1.25% wt/vol | 13 klm | 76 abc |
| 16. PINNACLE + CARGILL ISOCLEAR 55 | 2.5% wt/vol | 8 m | 69 efg |
| 17. PINNACLE + CARGILL CRGX 5290 | 1.25% wt/vol | 11 lm | 68 fg |
| 18. PINNACLE + CARGILL CRGX 5290 | 2.5% wt/vol | 18 ijk | 75 a–e |
| 19. PINNACLE + CARGILL 43/43 | 1.25% wt/vol | 19 ij | 72 b–g |
| 20. PINNACLE + CARGILL 43/43 | 2.5% wt/vol | 15 i–l | 74 a–f |
| 21. PINNACLE + CARGILL 63/43 | 1.25% wt/vol | 14 jkl | 70 d–g |
| 22. PINNACLE + CARGILL 63/43 | 2.5% wt/vol | 14 jkl | 78 ab |
| CARGILL 63/43 | wt/vol | | |
| $LSD_{0.05}$ | | | 6.1 |

EXAMPLE 4

Example 4 shows field studies in wheat using fructose and various herbicides.

TABLE 22

The effect of high fructose corn syrup on glufosinate-ammonium (LIBERTY) efficacy on wheat in a field study in 1997

| | | Control | | |
|---|---|---|---|---|
| Treatment | LIBERTY Rate | 7 DAT | 14 DAT | 21 DAT |
| | | ------(%)--------- | | |
| Untreated | | 0 | 0 | 0 |
| LIBERTY[a] | 0.26 lb/A | 51 | 61 | 33 |
| LIBERTY + ISOCLEAR 55 (1.25%) | 0.26 lb/A | 57 | 70 | 52 |
| LIBERTY + ISOCLEAR 55 (1.25%) + SCYTHE (1.0%) | 0.26 lb/A | 45 | 55 | 31 |
| LIBERTY + SCYTHE (1.0%) | 0.26 lb/A | 40 | 37 | 19 |
| LIBERTY + ISOCLEAR 55 (1.25%) + AMWAY 363566 P (1.25%) | 0.26 lb/A | 62 | 72 | 52 |
| LIBERTY + AMWAY 363566 P (1.25%) | 0.26 lb/A | 58 | 65 | 43 |
| $LSD_{0.05}$ | | 8 | 6 | 7 |

[a] All LIBERTY treatments received ammonium sulfate at 2%.

TABLE 23

The effect of high fructose corn syrup on glyphosate-isopropylamine (ACCORD) efficacy in a greenhouse study in 1997

| | Velvetleaf | Giant foxtail | Giant foxtail |
|---|---|---|---|
| | | Glyphosate Rate | |
| | 0.5 lb | 0.2 lb/A | 0.4 lb/A |
| Treatment | Control (14 DAT) | | |
| | ---------(%)--------- | | |
| Untreated | 0 | 0 | 0 |
| Glyphosate-isopropylamine | 0 | 0 | 51 |
| Glyphosate-isopropylamine + Fructose (1.25%) | 25 | 53 | 83 |
| Glyphosate-isopropylamine + A (1%)[a] | 63 | 53 | 100 |
| Glyphosate-isopropylamine + A (1%) + Fructose 1.25% | 70 | 83 | 100 |
| Glyphosate-isopropylamine + +B(1%) | 58 | 43 | 95 |
| Glyphosate-isopropylamine + B (1%) + Fructose (1.25%) | 67 | 33 | 100 |
| Glyphosate-isopropylamine + C (1%) | 23 | 10 | 38 |

TABLE 23-continued

The effect of high fructose corn syrup on
glyphosate-isopropylamine (ACCORD) efficacy
in a greenhouse study in 1997

| Treatment | Velvetleaf | Giant foxtail | Giant foxtail |
|---|---|---|---|
| | | Glyphosate Rate | |
| | 0.5 lb | 0.2 lb/A | 0.4 lb/A |
| | | Control (14 DAT) | |
| | ----------(%)---------- | | |
| Glyphosate-isopropylamine + C (1%) + Fructose (1.25%) | 34 | 43 | 78 |
| Glyphosate-isopropylamine + B (0.02%) | 23 | 0 | 33 |
| Glyphosate-isopropylamine + B (0.02%) + Fructose (1.25%) | 39 | 84 | 100 |
| $LSD_{0.05}$ | 11 | 7 | 8 |

[a]A and B are emulsifiers, C is a mineral oil.

EXAMPLE 6

Example 6 shows other monosaccharides (glucose, mannose) including chemically modified monosaccharides, can be used. (Isopropylamine salt glyphosate without adjuvants (ACCORD).

TABLE 24

| Treatments | Visual injury (14 DAT) Giant foxtail -------%------ |
|---|---|
| 1. Non-treated control | 0 |
| 2. ACCORD alone (0.2 lb/A) | 0 |
| 3. ACCORD + X-77 (0.25%) | 3 |
| 4. ACCORD + X-77 + Fructose (1.25%) | 78 |
| 5. ACCORD + X-77 + D-glucose (1.25%) | 68 |
| 6. ACCORD + X-77 + D-Mannose (1.25%) | 79 |
| 7. ACCORD + X-77 + DL-Glyceraldehyde (1.25%) | 40 |
| 8. ACCORD + X-77 + Dihydroxyacetone (1.25%) | 51 |
| 9. ACCORD + X-77 + 2-deoxy-D-glucose (1.25%) | 68 |
| 10. ACCORD + X-77 + Maltose (1.25%) | 44 |
| 11. ROUNDUP ULTRA (0.2 lb/A) | 11 |
| 12. ROUNDUP ULTRA + X-77 | 45 |

EXAMPLE 7

Example 7 shows that non-converted sources of fructose (soft drinks) can be used.

TABLE 25

| | Visual injury (14 DAT) | |
|---|---|---|
| Treatment | Velvetleaf | Giant foxtail |
| | ----------%---------- | |
| 1. Control | 0 | 0 |
| 2. LIBERTY (0.10 lb/A) | 49 | 4 |
| 3. LIBERTY + AMS (2%) | 79 | 21 |
| 4. LIBERTY + ISOCLEAR 55 (1.25%) | 41 | 63 |
| 5. LIBERTY + ISOCLEAR 55 + AMS | 81 | 96 |
| 6. LIBERTY + fructose (1.25%) | 43 | 68 |
| 7. LIBERTY + fructose + AMS | 80 | 87 |
| 8. LIBERTY + COKE (Classic) (11%) | 51 | 66 |
| 9. LIBERTY + COKE (Classic) + AMS | 80 | 93 |
| 10. LIBERTY + PEPSI (11%) | 46 | 73 |
| 11. LIBERTY + PEPSI + AMS | 80 | 95 |

It is intended that the foregoing description is only illustrative of the present invention and the present invention is limited only by the hereinafter appended claims.

We claim:

1. A composition which comprises an admixture:
   (a) a postemergence herbicide which is effective against weeds growing with or without a crop plant; and
   (b) an amount of a monosaccharide sufficient to potentiate the effect of the herbicide in killing the weeds without decreasing tolerance of the crop plant to the herbicide.

2. The composition of claim 1 comprising a surfactant which increases the killing of the weeds.

3. The composition of any one of claims 1 or 2 wherein the herbicide is an amino acid derivative.

4. The composition of claim 1 containing an adjuvant selected from the group consisting of a surfactant, an oil, an oil ester and mixtures thereof which increases the killing of the weeds.

5. In a method for killing weeds growing with a crop plant the improvement which comprises: applying a composition comprising in admixture, a postemergence herbicide which is effective against weeds growing with or without a crop plant; and an amount of a monosaccharide sufficient to potentiate the effect of the herbicide in killing the weeds without decreasing tolerance of the crop plant to the herbicide.

6. The method of claim 5 wherein the composition comprises a surfactant which increases the killing of the weeds.

7. The method of any one of claims 5 or 6 wherein the herbicide is an amino acid derivative.

8. The method of claim 5 wherein a surfactant and an oil, an oil ester and mixtures thereof increases the killing of the weeds.

9. A synergistic composition which comprises an admixture:
   (a) a postemergence herbicide which is effective against weeds growing with or without a crop plant; and
   (b) an amount of fructose sufficient to potentiate the effect of the herbicide in killing the weeds without decreasing tolerance of the crop plant to the herbicide.

10. The composition of claim 9 comprising a surfactant which increases the killing of the weeds.

11. The composition of any one of claims 9 or 10 wherein the herbicide is an amino acid derivative.

12. The composition of claim 9 comprising a surfactant and an oil, oil ester or adjuvant which increases the killing of the weeds.

13. In a method for killing weeds growing with a crop plant the improvement which comprises: applying a composition comprising in admixture, a postemergence herbicide which is effective against weeds growing with or without a crop plant; and an amount of fructose sufficient to potentiate the effect of the herbicide in killing the weeds without decreasing tolerance of the crop plant to the herbicide.

14. The method of claim 3 wherein the composition comprises a surfactant which increases the killing of the weeds.

15. The method of any one of claims 13 or 14 wherein the herbicide is an amino acid derivative.

16. The method of claim 13 wherein the composition comprises a surfactant and an oil, oil ester or adjuvant which increases the killing of the weeds.

17. A composition for killing weeds which comprises in admixture:
   (a) a postemergence herbicide which is effective against the weeds growing with or without a crop plant;
   (b) a surfactant which increases the killing of the weeds;
   (c) a metal ion binding agent; and
   (d) a monosaccharide to potentiate the effect of the herbicide in killing the weeds without decreasing tolerance of the crop plant to the herbicide.

18. The composition of claims 1 or 17 wherein the monosaccharide is provided by corn or soft drink syrup.

19. The composition of claim 18 wherein the corn syrup is between 1.25% and 11%.

20. The composition of claim 17 wherein the herbicide is an amino acid derivative.

21. The composition of claim 17 wherein the metal ion binding agent is ammonium sulfate, ammonium nitrate, a chelator and mixtures thereof.

22. The composition of any one of claims 17, 20 or 21 wherein the surfactant is non-ionic.

23. In a method for killing weeds growing with a crop plant, the improvement which comprises:
   applying an admixture of a postemergence herbicide which is effective against the weeds growing with or without a crop plant; a surfactant which increases the killing of the weeds; a metal ion binding agent to bind metal ions; and a monosaccharide to potentiate the effect of the herbicide in killing the weeds without decreasing tolerance of the crop plant to the herbicide.

24. The method of claim 23 wherein the monosaccharide is provided by corn or soft drink syrup.

25. The method of claim 24 wherein the corn syrup is between 1.25% and 11%.

26. The method of claim 23 wherein the herbicide is an amino acid derivative.

27. The method of claim 23 wherein the metal ion binding agent is selected from the group consisting of ammonium sulfate, ammonium nitrate, a chelator and mixtures thereof.

28. The method of any one of claims 23, 24, 25, 26 or 27 wherein the surfactant is non-ionic.

* * * * *